(12) United States Patent
Fowers et al.

(10) Patent No.: US 6,592,899 B2
(45) Date of Patent: Jul. 15, 2003

(54) PLA/PLGA OLIGOMERS COMBINED WITH BLOCK COPOLYMERS FOR ENHANCING SOLUBILITY OF A DRUG IN WATER

(75) Inventors: Kirk Dee Fowers, Layton, UT (US); Gaylen M. Zentner, Salt Lake City, UT (US); Chung Shih, Sandy, UT (US); Ai-Zhi Piao, Salt Lake City, UT (US)

(73) Assignee: Macromed Incorporated, Sandy, UT (US)

( * ) Notice: Subject to any disclaimer, the term of this patent is extended or adjusted under 35 U.S.C. 154(b) by 0 days.

(21) Appl. No.: 09/971,082

(22) Filed: Oct. 3, 2001

(65) Prior Publication Data

US 2003/0068377 A1 Apr. 10, 2003

(51) Int. Cl.⁷ ............................ A61K 9/14; A61K 9/70; A61F 6/06; A61F 13/00
(52) U.S. Cl. .................. 424/486; 424/426; 424/444; 424/430; 424/434; 424/449; 424/484; 525/411; 525/413; 525/415
(58) Field of Search ................. 525/411, 413, 525/415; 528/354, 359; 424/486, 426, 428, 430, 434, 449, 451, 464, 443

(56) References Cited

U.S. PATENT DOCUMENTS

| | | | |
|---|---|---|---|
| 4,745,160 A | * 5/1988 | Churchill et al. | ........... 525/415 |
| 5,410,016 A | 4/1995 | Hubbell et al. | |
| 5,449,513 A | 9/1995 | Yokoyama et al. | |
| 5,510,103 A | 4/1996 | Yokoyama et al. | |
| 5,514,380 A | 5/1996 | Song et al. | |
| 5,543,158 A | * 8/1996 | Gref et al. | ................... 424/501 |
| 5,620,700 A | 4/1997 | Berggren et al. | |
| 5,702,717 A | 12/1997 | Cha et al. | |
| 5,725,841 A | 3/1998 | Duan et al. | |
| 5,780,044 A | 7/1998 | Yewey et al. | |
| 5,843,891 A | 12/1998 | Sherman | |
| 5,922,340 A | 7/1999 | Berde et al. | |
| 5,929,177 A | 7/1999 | Kataoka et al. | |
| 5,942,241 A | 8/1999 | Chasin et al. | |
| 6,004,573 A | * 12/1999 | Rathi et al. | ................... 424/426 |
| 6,042,811 A | 3/2000 | Duan et al. | |
| 6,060,518 A | 5/2000 | Kabanov et al. | |
| 6,117,949 A | 9/2000 | Rathi et al. | |
| 6,126,919 A | 10/2000 | Stefely et al. | |
| 6,201,065 B1 | 3/2001 | Pathak et al. | |
| 6,201,072 B1 | 3/2001 | Rathi et al. | |

FOREIGN PATENT DOCUMENTS

| | | |
|---|---|---|
| EP | 0 397 307 | 3/1990 |
| EP | 0 552 802 | 1/1993 |
| EP | 0 583 955 | 8/1993 |

OTHER PUBLICATIONS

B.G. Yu, T. Okano, K. Kataoka, G. Kwon—Polymeric micelles for drug delivery; solubilization and haemolytic activity of amphotercin B—*Journal of Controlled Release* 53(1998) 131–136.

Marie–Christine Jones, Jean–Christophe Leroux—Polymeric micelles—a new generation of colloidal drug carriers—*European Journal of Pharmaceutics and Biopharmaceutics* 48 (1999) 101–111.

Xichen Zhang, John K. Jackson, Helen M. Burt—Development of amphiphilic diblock copolymers as micellar carriers of taxol—*International Journal of Pharamceutics* 132 (1996) 195–206.

* cited by examiner

*Primary Examiner*—Thurman K. Page
*Assistant Examiner*—Blessing Fubara
(74) *Attorney, Agent, or Firm*—Thorpe North & Western, LLP

(57) ABSTRACT

Polymeric compositions having improved capability of solubilizing a drug in a hydrophilic environment to form a solution, comprising: a biodegradable polyester oligomer; and biodegradable AB-type, ABA-type, or BAB-type block copolymers are disclosed. The copolymers are comprised of about 50.1 to 65% by weight of a biodegradable, hydrophobic A polymer block comprising a biodegradable polyester, and about 35 to 49.9% by weight of a hydrophilic B polymer block comprising a polyethylene glycol (PEG), and wherein the block copolymer has a weight averaged molecular weight of between 2400 to 4999. The biodegradable polyester oligomer of said composition is within a range of 0.01% to 30% by weight of the total polymer mixture, and the content of the biodegradable AB-type, ABA-type, or BAB-type block copolymer is within a range of 70% to 99.99% by weight of the total polymer mixture.

79 Claims, No Drawings

PLA/PLGA OLIGOMERS COMBINED WITH BLOCK COPOLYMERS FOR ENHANCING SOLUBILITY OF A DRUG IN WATER

FIELD OF THE INVENTION

The present invention relates to compositions comprising biodegradable polyester oligomers, and particularly PLA/PLGA oligomers, and water soluble, low molecular weight, biodegradable block copolymers and their use for solubilizing a drug in a hydrophilic environment. Particularly, this invention relates to the use of biodegradable polyester oligomers, and particularly PLA/PLGA oligomers to enhance the solubilizing performance of biodegradable tri-block and diblock copolymers that are based on biodegradable polyester and polyethylene glycol (PEG) blocks, which are used as solubilizing agents at physiologically relevant temperatures (temperatures <45° C.).

BACKGROUND OF THE INVENTION

Many important drugs have limited solubility in water, especially hydrophobic drugs. In order to attain the full expected therapeutic effect of such drugs, it is usually required that a solubilized form of the drug be administered to a patient. Recently, many peptide/protein drugs, effective for a variety of therapeutic applications, have become commercially available through advances in recombinant DNA and other technologies. Many peptide drugs are of limited solubility and/or stability in conventional liquid carriers and are therefore difficult to formulate and administer.

A number of methods for solubilizing drugs have been developed that are based on the use of solvents or cosolvents, surfactants, complexation agents (e.g., cyclodextrins, or nicotinamides), or complex drug carriers (e.g., liposomes). Each of the above methods has one or more drawbacks. Conventional surfactants and complexing agents have drawbacks of toxicity, and rapid precipitation of the solubilized drugs once administered to the patient or when otherwise diluted in an aqueous environment. Solvents and cosolvents can be toxic and irritating when injected into humans, such that the use of this solubilization approach is largely restricted to therapies for acute, life threatening diseases where medical experts are constantly in attendance to administer palliative treatments to counteract the adverse effects of the solvents/cosolvents. Water miscible solvents/cosolvents also possess the undesirable feature of allowing the drug to rapidly precipitate when an aqueous environment is contacted. Complex drug carriers, such as liposomes have limited utility due to the unstable nature of the carrier particles and the preferential uptake and localization of liposomal drugs to the reticuloendothelial system, namely, the liver and spleen.

Amphiphilic block copolymers are effective drug carriers that solubilize drugs and particularly hydrophobic drugs into an aqueous environment. For example, there are reports of amphiphilic block copolymers exhibiting self-association properties. EP No. 0 397 307 A2 (See also EP No. 0 583 955 A2 and EP No. 0 552 802 A2.) discloses polymeric micelles of an AB-type amphiphilic diblock copolymer which contains poly(ethylene oxide) as the hydrophilic B-block and poly(amino acids) as the hydrophobic A-block, wherein therapeutically active agents are covalently bonded to the A-block. Although this polymeric micelle is provided as a means of administering a hydrophobic drug, it is highly disadvantageous because it requires the introduction of functional groups into the block copolymer, and the covalent coupling of the drug to the polymeric carrier which creates new chemical entities that are impossible to fully characterize and reproducibly manufacture.

U.S. Pat. No. 4,745,160 discloses water insoluble, amphiphilic, non-crosslinked linear, branched or graft block copolymers having polyethylene glycol as the hydrophilic component and poly(D-, L-, or D, L-lactic acids) as the hydrophobic components. Although the block copolymer is described as an effective dispersing agent or suspending agent for a hydrophobic drug, the block copolymer is insoluble in water and has a molecular weight of 5,000 daltons or more. Furthermore, the hydrophilic component is at least 50% by weight based on the weight of the block copolymer and the molecular weight of the hydrophobic component is 5,000 or less. In the preparation process, a water-miscible and lyophilizable organic solvent is used. When a mixture of the polymer, the drug and an organic solvent are combined with water, precipitates are formed and then the mixture is directly lyophilized to form particles. Therefore, when this particle is dispersed in water, it forms a suspension of macroscopically visible particles.

U.S. Pat. No. 5,543,158 discloses nanoparticles or microparticles formed from a water-insoluble block copolymer consisting essentially of poly(alkylene glycol) and poly(lactic acid). The molecular weight of the block copolymer is high and the copolymer is insoluble in water. In the nanoparticle or microparticle, the biodegradable moieties of the copolymer are in the core of the nanoparticle or microparticle and the poly(alkylene glycol) moieties are on the surface of the nanoparticle or microparticle in an amount effective enough to decrease uptake of the nanoparticle or microparticle by the reticuloendothelial system. Nanoparticles are prepared by dissolving the block copolymer and drug in an organic solvent, forming an o/w emulsion by sonication or stirring, and collecting the nanoparticles containing the drug following precipitation. It does not provide for the solubilization of hydrophobic drugs. The nanoparticles are solid particles that are suspended in water.

Currently there are few synthetic or natural polymeric materials that can be used for the controlled delivery of drugs, including peptide and protein drugs, because of strict regulatory compliance requirements such as biocompatibility and low toxicity, having a clearly defined degradation pathway, and safety of the polymers and degradation products. The most widely investigated and advanced biodegradable polymers in regard to available toxicological and clinical data are the aliphatic poly(α-hydroxy acids), such as poly(D-, L-, or D, L-lactic acid) (PLA) and poly(glycolic acid) (PGA) and their copolymers (PLGA). These polymers are commercially available and are presently used as bioresorbable sutures. FDA-approved microsphere systems for controlled release of leuprolide acetate (Lupron Depot™) and human growth hormone (Nutropin Depot™) are also based on PLGA copolymers. Based on this history of use, PLGA copolymers have been the materials of choice in the initial design of parenteral controlled release drug delivery systems using a biodegradable carrier.

Even though there has been some limited success, PLA, PGA, and PLGA polymers present problems as drug carriers that are associated with their physicochemical properties and attendant methods of fabrication. Hydrophilic macromolecules, such as proteins may not readily diffuse through hydrophobic matrices of these polymers. Drug loading and device fabrication using PLA and PLGA often requires use of toxic organic solvents or high temperatures that denature and degrade many drugs. Also, the solid and rigid geometries of the administered solid dosage form may mechanically induce tissue irritation and damage.

There has been no previous disclosure of a composition comprising biodegradable polyester oligomers, and particularly PLA/PLGA oligomers, and low molecular weight, biodegradable triblock or diblock copolymers having a high weight percentage (at least 50 weight percent) of hydrophobic block(s) as solubilizing agents for drugs, or hydrophobic drugs in particular. Accordingly, the present invention represents improved solubilizers that minimize or are free of the problems mentioned above. It has been unexpectedly demonstrated that compositions of biodegradable polyester oligomers, and particularly PLA/PLGA oligomers and amphiphilic, biodegradable triblock or diblock copolymers are more effective in solubilizing drugs and especially hydrophobic drugs than using the triblock or diblock copolymers alone. Biodegradable polyester oligomers, and particularly PLA/PLGA oligomers increase the solubilization capacity and stability of the drug solution thereby enhancing the efficiency and therapeutic effects of the drug. Controlling the molecular weights, compositions, and relative ratios of the hydrophilic and hydrophobic blocks of the copolymers, the composition and molecular weight of biodegradable polyester oligomers, and particularly PLA/PLGA oligomers, and the relative amounts of copolymer and oligomer can optimize such drug solubilizing effects.

SUMMARY OF THE INVENTION

The present invention provides a biodegradable polymeric composition capable of solubilizing a drug, and particularly a hydrophobic drug, into a hydrophilic environment, and may be used in preparing a pharmaceutically effective formulation of such drugs.

The present invention also provides a method for effectively solubilizing a drug, particularly a hydrophobic drug, into a hydrophilic environment and a method for effectively administering such a drug at physiologically relevant temperatures (temperatures <45° C.) to animals by a means such as parenteral, ocular, inhalation, transdermal, vaginal, buccal, transmucosal, transurethral, rectal, nasal, oral, peroral, pulmonary, topical or aural means, although any desired route of administration may be compatible with the present invention.

The solubilizing agent of the present invention comprises biodegradable polyester oligomers, and particularly PLA/PLGA oligomers having a weight averaged molecular weight of between 400 and 10,000, and biodegradable ABA-type or BAB-type triblock copolymers, or AB-type diblock copolymers having a weight averaged molecular weight of between 2400 and 4999. The block copolymers have 50.1 to 65% by weight of the hydrophobic A polymer block(s) comprising biodegradable polyesters and 35 to 49.9% by weight of the hydrophilic B polymer block(s) consisting of polyethylene glycol (PEG). Preferably, the biodegradable polyester comprising the A-block of the copolymers, and the biodegradable polyester oligomers are synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, δ-hydroxy valeric acid, hydroxybutyric acids, malic acid, and copolymers thereof. More preferably, the biodegradable polyester is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof. Most preferably, the biodegradable polyester is synthesized from monomers selected from the group consisting of D, L-lactide, D-lactide, L-lactide, D, L-lactic acid, D-lactic acid, L-lactic acid, glycolide, glycolic acid, and copolymers thereof.

Polyethylene glycol (PEG) is also sometimes referred to as poly(ethylene oxide) (PEO) or poly(oxyethylene) when incorporated into a block copolymer, and the terms can be used interchangeably for the purposes of this invention.

In the case where the A-block(s) and oligomer are PLA/PLGA polyesters, the lactate content is between about 20 to 100 mole percent, preferably between about 50 to 100 mole percent. The glycolate content is between about 0 and 80 mole percent, preferably between about 0 to 50 mole percent.

The compositions of the present invention are very effective in solubilizing drugs and particularly hydrophobic drugs into water thus facilitating administration of a uniform and accurate dose at physiologically relevant temperatures (temperatures <45° C.) that may then, in many cases, enhance the therapeutic effect of the drug. For purposes of this invention, the description of the solubilized drug as a solution includes solutions of the drug in the solubilizing media at physiologically relevant temperatures (temperatures <45° C.). Solubilized drugs and drug solutions includes all free flowing forms of the compositions comprising the oligomers and copolymers of the present invention, water and drug(s) where the drug(s) is dissolved. All forms can act to facilitate administration of the drug and enhance the therapeutic effect. Such therapeutic effects may be optimized by controlling the copolymer molecular weights, compositions, and the relative ratios of the hydrophilic and hydrophobic blocks, ratios of drug to copolymer, ratios of copolymer to oligomer, and both drug and copolymer concentrations in the final administered dosage form. Additional advantages of this invention will become apparent from the following detailed description of the various embodiments.

DETAILED DESCRIPTION OF THE INVENTION

This invention is not limited to the particular configurations, process steps, and materials disclosed herein, as such configurations, process steps, and materials may vary somewhat. It is also to be understood that the terminology employed herein is used for the purpose of describing particular embodiments only, and is not intended to be limiting since the scope of the present invention will be limited only by the appended claims and equivalents thereof.

In this specification and the appended claims, the singular forms "a," "an," and "the" include plural references unless the context clearly dictates otherwise. Thus, for example, reference to a composition for delivering "a drug" includes reference to two or more drugs. In describing and claiming the present invention, the following terminology will be used in accordance with the definitions set out below.

"Effective amount" means an amount of a drug, biologically active agent or pharmacologically active agent that provides the desired local or systemic effect.

"Polymer solution," "aqueous solution" and the like, when used in reference to a biodegradable block copolymer contained in such a solution, shall mean a water, i.e. aqueous, based composition having such block copolymer and biodegradable polyester oligomers, or particularly PLA/PLGA oligomer dissolved therein at a functional concentration. Polymer solution includes all free flowing forms of the composition comprising the oligomers and copolymers of the present invention and water. Polymer solutions act to solubilize the drug in a form that is acceptable for administration at physiologically relevant temperatures (temperatures <45° C.).

"Polymeric drug delivery composition" shall mean the combination of drug, oligomer, and block copolymer.

"Aqueous solution" shall include water without additives or aqueous solutions containing additives or excipients such as pH buffers, components for tonicity adjustment, antioxidants, preservatives, drug stabilizers, etc., as commonly used in the preparation of pharmaceutical formulations.

"Drug formulation" shall include all combinations of drug with polymer, for example polymer solutions that are mixed with drug to form drug solutions, as well as mixtures of undissolved polymer with drug, i.e. polymeric drug delivery compositions, that are subsequently dissolved into an aqueous environment to form a drug solution.

"Drug solution", "solubilized drug", "dissolved drug", "solution" and all other terms that refer to drug in a solution or dissolved state includes solutions of the drug in the solubilizing media at physiologically relevant temperatures (temperatures <45° C.). Solubilized drugs and drug solutions includes all free flowing forms of the compositions comprising the oligomers and copolymers of the present invention, water and drug(s) where the drug(s) is dissolved. All forms can act to facilitate administration of the drug and enhance the therapeutic effect.

"Administration" is the means by which drug formulations are presented to humans and animals in effective amounts, and includes all routes for dosing or administering drugs, whether self-administered or administered by medical practitioners.

"Parenteral" shall mean administration by means other than through the digestive tract such as intramuscular, intraperitoneal, intra-abdominal, subcutaneous, intrathecal, intrapleural, intravenous and intraarterial means.

"Biodegradable" means that the block copolymer or oligomer can chemically break down or degrade within the body to form nontoxic components. The rate of degradation can be the same or different from the rate of drug release.

"Drug" shall mean any organic or inorganic compound or substance having biological or pharmacological activity and adapted or used for a therapeutic purpose.

"Hydrophobic drug" shall mean any organic or inorganic compound or substance having biological or pharmacological activity and adapted or used for a therapeutic purpose having a water solubility less than 100 mg/mL "Peptide," "polypeptide," "oligopeptide" and "protein" shall be used interchangeably when referring to peptide or protein drugs and shall not be limited as to any particular molecular weight, peptide sequence or length, field of bioactivity or therapeutic use unless specifically stated.

"PLGA" shall mean a copolymer or copolymer radicals derived from the condensation copolymerization of lactic acid and glycolic acid, or, by the ring opening polymerization of lactide and glycolide. The terms lactic acid and lactate are used interchangeably; glycolic acid and glycolate are also used interchangeably.

"PLA" shall mean a polymer derived from the condensation of lactic acid or by the ring opening polymerization of lactide.

"Biodegradable polyesters" refer to any biodegradable polyesters, which are preferably synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, δ-hydroxy valeric acid, hydroxybutyric acids, malic acid, and copolymers thereof.

The present invention is based on the discovery of combining biodegradable polyester oligomers, and particularly PLA/PLGA oligomers having a weight averaged molecular weight of between 400 and 10,000, with ABA-type, BAB-type, or AB-type block copolymers, where the A-blocks are relatively hydrophobic polymer blocks comprising a biodegradable polyester, and the B-blocks are relatively hydrophilic polymer blocks comprising polyethylene glycol (PEG), having a hydrophobic content of between about 50.1 to 65% by weight and an overall block copolymer weight-averaged molecular weight of between about 2400 and 4999, and which are water soluble and capable of enhancing the solubility of drugs and hydrophobic drugs in particular, in water, to form a drug solution. It is also within the scope of the invention to include compositions where the drug is solubilized by the copolymer in an aqueous environment, yet the desired dose of the drug exceeds even this enhanced solubility state, and the final formulation of the drug has the visual appearance of a suspension or other dispersed condition, where a portion of the total drug load is dissolved and a portion of the total drug load is suspended or dispersed. With such high hydrophobic content in the block copolymers it is unexpected that such block copolymers would be water soluble. It is also an unexpected discovery that the composition of the present invention can significantly increase the water solubility and the stability of the drug solution. It is also surprising that inclusion in the present invention of an additional hydrophobic agent, i.e. biodegradable polyester oligomers, and particularly PLA/PLGA oligomers, further enhances the solubilization and the stability of drug solutions. Therefore, the composition of the present invention can be used as a solubilizing agent for the delivery of drugs and especially hydrophobic drugs, and, when administered, the hydrophobic biodegradable oligomers and polymer blocks decompose, in vivo, into non-toxic molecules. A drug may be delivered to a human or a warm blooded animal much more effectively as an aqueous solution with the biodegradable solubilizing compositions of the present invention, thus facilitating administration of a uniform and accurate dose which may in many cases enhance the therapeutic effect of the drug.

Basic to the present invention is the utilization of a block copolymer having hydrophobic A-block segments and hydrophilic B-block segments and biodegradable polyester oligomers, particularly PLA/PLGA oligomers. Generally the block copolymer will be an ABA-type or BAB-type triblock or AB-type diblock copolymer.

Both ABA-type and BAB-type triblock copolymers may be synthesized by ring opening polymerization, or condensation polymerization according to reaction schemes disclosed in U.S. Pat. Nos. 6,004,573, 6,117,949 and 6,201,072 the contents of which are fully incorporated herein by reference.

The block copolymers and biodegradable polyester oligomers, and particularly PLA/PLGA oligomers that have utility as disclosed herein meet the criteria summarized in Tables 1 and 2, respectively, namely having compositional make-up within the indicated ranges that result in block copolymers that demonstrate the desired dissolution when exposed to water. For purposes of disclosing molecular weight parameters, all reported molecular weight values are based on measurements by $^1$H-NMR or GPC (gel permeation chromatography) analytical techniques. The reported weight averaged molecular weights and number averaged molecular weights were determined by GPC and $^1$H-NMR, respectively. The reported lactide/glycolide ratios were calculated from $^1$H-NMR data. GPC analysis was performed on a Styragel HR-3 column, or equivalent, calibrated with PEG standards using RI detection and chloroform as the eluent, or on a combination of Phenogel, mixed bed, and 500 Å columns calibrated with PEG standards using RI detection and tetrahydrofuran as the eluent for the ABA and BAB triblock copolymers. The reported weight averaged molecular weights determined by GPC for biodegradable polyester oligomers, and particularly PLA/PLGA oligomers were conducted using an identical method with polystyrene standards. $^1$H-NMR spectra were taken in $CDCl_3$ on a Bruker 200 MHz instrument.

TABLE 1

Block Copolymer Specifications

| | |
|---|---|
| Total weight averaged molecular weight: | 2400 to 4999 |
| PEG content: | 35 to 49.9% by weight |
| Total polyester content: | 50.1 to 65% by weight |
| Lactate content: (in cases where polyester is PLA or PLGA) | 20 to 100 mole percent |
| Glycolate content: (in cases where polyester is PLA or PLGA) | 0 to 80 mole percent |
| Neat Polymer Behavior: | high viscosity liquid |

TABLE 2

Oligomer Specifications

| | |
|---|---|
| Total weight averaged molecular weight: | 400 to 10,000 |
| Lactate content: (in cases where polyester is PLA or PLGA) | 20 to 100 mole percent |
| Glycolate content: (in cases where oligomer is PLA or PLGA) | 0 to 80 mole percent |
| Neat Oligomer Behavior: | can mix with copolymer |

The biodegradable polyester comprising the A-block of the copolymers, and the biodegradable polyester oligomers are synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, δ-butyrolactone, δ-hydroxy butyric acid, δ-valerolactone, δ-hydroxy valeric acid, hydroxybutyric acids, malic acid, and copolymers thereof. The biodegradable polyester of the A-block of the copolymers can be the same or different from the biodegradable polyester of the oligomers. The hydrophilic B-block segment is preferably polyethylene glycol (PEG) having a weight averaged molecular weight of between about 1000 and 2000.

ABA-type and BAB-type triblock copolymers, AB-type diblock copolymers, and biodegradable polyester oligomers, and particularly PLA/PLGA oligomers may be synthesized by ring opening polymerization, or condensation polymerization. Additionally, the B-blocks may in certain instances be coupled to the A-blocks by ester or urethane links and the like. Condensation polymerization and ring opening polymerization procedures may be utilized as may the coupling of a monofunctional hydrophilic B block to either end of a difunctional hydrophobic A block in the presence of coupling agents such as isocyanates. Furthermore, coupling reactions may follow activation of functional groups with activating agents, such as carbonyl diimidazole, succinic anhydride, N-hydroxy succinimide and p-nitrophenyl chloroformate and the like.

The hydrophilic B-block is formed from PEG or derivatized PEG of an appropriate molecular weight. PEG was chosen as the hydrophilic B-block because of its unique biocompatibility, nontoxic properties, hydrophilicity, solubilization properties, and rapid clearance from a patient's body.

The hydrophobic A-blocks and biodegradable polyester oligomers are utilized because of their biodegradable, biocompatible, and solubilization properties. The in vitro and in vivo degradation of hydrophobic, biodegradable polyester A-blocks and biodegradable polyester oligomers are well understood and the degradation products are readily metabolized and/or eliminated from the patient's body.

Surprisingly, the total weight percentage of the hydrophobic polyester A-block, relative to that of the hydrophilic B-block, is high, e.g. between about 50.1 to 65% by weight of A-block(s), yet the resulting block copolymer retains the desirable water solubility. The total weight percentage of the biodegradable polyester oligomers, and particularly PLA/PLGA oligomers relative to the triblock or diblock copolymer is between 0.01% and 30% by weight, further increasing the hydrophobic to hydrophilic ratio of the copolymer and oligomer mixture, thus further increasing drug solubility and stability in the formulations. It is an unexpected discovery that a block copolymer with such a large proportion of hydrophobic component plus an additional hydrophobic contribution from the biodegradable polyester oligomers would be not only water soluble, but also greatly enhance the water solubility of hydrophobic drugs. It is believed that this desirable solubility characteristic is made possible by maintaining the overall weight averaged molecular weight of the entire triblock or diblock copolymer between 2400 and 4999, and the overall weight averaged molecular weight of the biodegradable polyester oligomers, and particularly PLA/PLGA oligomer between 400 and 10,000. Thus, water soluble biodegradable block copolymers capable of enhancing the water solubility of drugs and hydrophobic drugs are prepared wherein the hydrophilic B-block(s) make up about 35 to 49.9% by weight of the copolymer and the hydrophobic A-block or blocks make up about 50.1 to 65% by weight of the copolymer. The weight percentage of biodegradable polyester oligomers, and particularly PLA/PLGA oligomers remained functional if the range was between 0.01% and 30% of the total polymer weight, where the total polymer weight is the combined weight of oligomer plus block copolymer.

The concentration in an aqueous solution at which the block copolymers are apparently soluble and capable of enhancing the water solubility of a drug may be considered as the functional concentration. Generally speaking, block copolymer concentrations of as low as 1% and up to about 50% by weight in aqueous solvents are functional. However, concentrations in the range of about 5 to 40% are preferred and concentrations in the range of about 10 to 30% by weight are most preferred. In a similar manner, the concentration of the biodegradable polyester oligomers, and particularly PLA/PLGA oligomer can be as low as 0.01% and as high as 30% of the total polymer weight and remain functional. However, concentrations of 5 to 15% of the total polymer weight are most preferred.

Drugs that may be solubilized or dispersed by the block copolymers of the present invention can be any bioactive agent, but particular advantage is achieved with bioactive agents having limited solubility or dispersibility in an aqueous or hydrophilic environment, or any bioactive agent that requires enhanced solubility or dispersibility. Without limiting the scope of the present invention, suitable drugs include those drugs presented in Goodman and Gilman's "The Pharmacological Basis of Therapeutics" 9th Edition or The Merck Index 12th Edition. Both volumes list drugs suitable for numerous types of therapeutic applications, including drugs in the following categories:drugs acting at synaptic and neuroeffector junctional sites, drugs acting on the central nervous system, drugs that influence inflammatory responses, drugs that affect the composition of body fluids, drugs affecting renal function and electrolyte metabolism, cardiovascular drugs, drugs affecting gastrointestinal function, drugs affecting uterine motility, chemotherapeutic agents for parasitic infections, chemotherapeutic agents for microbial diseases, antineoplastic agents, immunosuppressive agents, drugs affecting the blood and blood-forming organs, hormones and hormone antagonists, dermatological agents, heavy metal antagonists, vitamins and nutrients, vaccines, oligonucleotides and gene therapies.

Incorporating or solubilizing one or more drugs mentioned in the above categories with the mixtures of block copolymers and oligomers of the present invention to form an aqueous solution or dispersion can be achieved by simply adding the drug to an aqueous mixture of copolymer and oligomer, or by mixing the drug with the neat copolymer and oligomer and thereafter adding water to form a solution or dispersion.

The mixture of the biodegradable copolymers and oligomers with peptide/protein drugs, and/or other types of drugs, may be prepared as an aqueous drug delivery liquid that may be in the form of a solution or dispersion. This aqueous drug delivery liquid is then administered parenterally, topically, transdermally, transmucosally, inhaled, or inserted into a cavity such as by ocular, vaginal, transurethral, rectal, nasal, oral, peroral, buccal, pulmonary or aural administration to a patient. Many of the aqueously solubilized formulations prepared by implementing the present invention may be diluted in an i.v. bag or by other means, and administered to a patient, without precipitation of the drug for an extended period. The maximum concentration of the drug in solution and the period and conditions during which the drug remains in solution is often prolonged by addition of the biodegradable polyester oligomers, and particularly PLA/PLGA oligomers as compared to the ABA-, BAB-, or AB-type biodegradable block copolymers alone. This system will cause minimal toxicity and minimal mechanical irritation to the surrounding tissue due to the biocompatibility of the materials and the free flowing nature of the system at physiological temperatures (<45° C.). The A-blocks and biodegradable polyester oligomers, and particularly PLA/PLGA oligomers will be hydrolyzed or biodegraded to corresponding monomers, for example lactic acid and glycolic acid, within a specific time interval.

A distinct advantage to the compositions of this invention lies in the ability of the block copolymer to increase the solubility of many drug substances that is further enhanced by the addition of biodegradable polyester oligomers, and particularly PLA/PLGA oligomers. The combination of the hydrophobic A-block(s) and hydrophilic B-block(s) renders the block copolymer amphiphilic in nature. This is particularly advantageous in the solubilization of hydrophobic or poorly water soluble drugs such as cyclosporin A and paclitaxel. What is surprising is the degree of solubilization into an aqueous environment of most, if not all, drugs since the block copolymer's A-block(s) and the biodegradable polyester oligomers, and particularly PLA/PLGA oligomers are relatively hydrophobic. However, as already discussed, even though hydrophobic polymer block(s) are present in substantial amounts, the block copolymers per se are water soluble and it has been found that there is an additional increase in drug solubility with the addition of biodegradable polyester oligomers, and particularly PLA/PLGA oligomers.

Another advantage to the composition of the invention lies in the ability of PLA/PLGA oligomers to increase the solution stability and the chemical stability of many drug substances dissolved in the solution. Various mechanisms for the degradation of drugs, that lead to a drug's chemical instability, have been observed to be inhibited when the drug is in the presence of the composition of the present invention. For example, paclitaxel and cyclosporin A are substantially stabilized in the aqueous polymer composition of the present invention relative to certain aqueous solutions of these same drugs in the presence of organic co-solvents. This stabilization effect on paclitaxel and cyclosporin A is but illustrative of the effect that can be achieved with many other drug substances.

The biodegradable polymeric compositions of the present invention act as solubilizing agents for drugs. In one possible configuration, a dosage form comprised of a solution of the block copolymer and oligomers that contains dissolved drug is administered to the body. Before administration, the drug solution may be freeze-dried for long-term storage, and the lyophilized biodegradable polymeric drug composition may be restored to its original solution by using water or other aqueous liquid.

The only limitation as to how much drug can be dispersed in the oligomer and water soluble, biodegradable block copolymer mixtures of the present invention is one of functionality, namely, the drug:copolymer ratio may be increased until the properties of the mixture are adversely affected to an unacceptable degree, or until the properties of the system are adversely affected to such a degree as to make administration of the system unacceptably difficult. Generally speaking, it is anticipated that in most instances where dissolution is desired, the drug will make up between about $10^{-6}$ to about 100 percent by weight of the total polymer weight (copolymer+oligomer) with ranges of between about 0.001% to 25% by weight being most common. For example, drug present at 100% by weight of the copolymer means the drug and copolymer are present in equal amounts (i.e., equal weights). Generally speaking, it is anticipated that in most instances where dispersion is desired, the upper drug copolymer ratio could substantially exceed the range noted above for dissolution. These ranges of drug loading are illustrative and will include most drugs that may be utilized in the present invention. However, such ranges are not limiting to the invention should drug loadings outside this range be functional and effective.

The present invention thus provides a biodegradable polymeric solubilizing agent for drugs and preferably hydrophobic drugs. The drug solution formed with the biodegradable polymeric solubilizing agent of the present invention has desirable physical stability, therapeutic efficacy, and toxicology.

In order to illustrate preferred embodiments of this invention, the synthesis of various low molecular weight AB-type, ABA-type or BAB-type block copolymers was accomplished and consisted of 50.1 to 65% by weight hydrophobic A-blocks (biodegradable polyesters), and 35 to 49.9% by weight hydrophilic B-block (polyethylene glycol "PEG"). The object was the preparation of ABA or BAB triblock or AB diblock copolymers having weight averaged molecular weights of about 2400 to 4999. The ability of PLA/PLGA oligomers to enhance the drug solubilizing functionality of the block copolymers described above was examined by preparation of PLA/PLGA oligomers with a weight averaged molecular weight between 400 and 10,000 daltons. The oligomers were mixed with copolymer to a final percentage of 0.01% to 30% of the total polymer mixture's weight. In the case where each A-block and PLA/PLGA oligomer consist of a biodegradable polyester synthesized from monomers selected from the group consisting of D, L-lactide, D-lactide, L-lactide, D, L-lactic acid, D-lactic acid, L-lactic acid, glycolide, or glycolic acid, the composition of the A-block and PLA/PLGA oligomers was about 20 to 100 mole percent lactate and 0 to 80 mole percent glycolate.

The following are examples that illustrate preferred embodiments of the invention but are intended as being representative only.

EXAMPLE 1

Synthesis of the ABA-Type Triblock Copolymer PLGA-PEG-PLGA by Ring Opening Copolymerization PEG (Mw=1450; 476.2 g) was dried under vacuum (1 mmHg) at 130° C. for 5 hours. D, L-lactide (412.9 grams) and glycolide (110.9 grams) were added to the flask and heated to 145° C. to afford a homogenous solution. Polymerization was initiated by the addition of 250 mg stannous octoate to the reaction mixture. After maintaining the reaction for five hours at 145° C., the reaction was stopped and the flask was cooled to room temperature. Unreacted lactide and glycolide were removed by vacuum distillation. The raw copolymer residue was a high viscosity liquid. The copolymer was purified by dissolving in water to afford a 25% solution and stirred overnight at room temperature, followed by elevating the solution temperature to 70° C. to precipitate the polymer. Excess water was removed by freeze drying. The resulting PLGA-PEG-PLGA copolymer had a weight averaged molecular weight (Mw) of 3855 as measured by GPC. The GPC was performed on two Phenogel columns (300×7.8), 500 Å, and a mixed bed connected in series. Mobile phase was tetrahydrofuran. Calibration was with PEG standards. Detection was by refractive index.

EXAMPLE 2

Following the basic procedure outlined in Example 1, other triblock copolymers were synthesized using PEG (Mw=1450, or 2000) with various lactide and/or glycolide content. The properties of these triblock copolymers were listed in the following table:

TABLE 3

Example ABA Block Copolymers with Solubilizing Enhancing Function

| Entry | PEG Molecular Weight | PLGA/PEG or PLA/PEG weight Ratio | LA:GA (mole ratio) | Solubilizing Enhancing Function |
|---|---|---|---|---|
| 1 | 1450 | 1.1 | 75:25 | yes |
| 2 | 1450 | 1.38 | 75:25 | yes |
| 3 | 1450 | 1.65 | 75:25 | yes |
| 4 | 1450 | 1.1 | 100:0 | yes |
| 5 | 2000 | 1.1 | 50:50 | yes |
| 6 | 2000 | 1.1 | 100:0 | yes |

It was noted that all of the polymers listed in the above table possessed the property of enhancing solubility of drugs and particularly hydrophobic drugs. Hence, both PLGA-PEG-PLGA and PLA-PEG-PLA triblocks were prepared and the results were summarized in this example.

EXAMPLE 3

Synthesis of an ABA-Type PLGA-PEG-PLGA Triblock Copolymer by Condensation Copolymerization Into a three necked flask, equipped with a nitrogen inlet, thermometer, and distillation head for removal of water, was placed D, L-lactic acid (360 gram) and glycolic acid (96.7 gram). The reaction mixture was heated at 160° C. under nitrogen, with stirring, for three days. The resulting PLGA copolymer had a weight averaged molecular weight (Mw) of 8800.

The PLGA copolymer (165 gram) was mixed with PEG (Mw=1450; 150 grams) and was heated in a flask at 160° C. under a nitrogen atmosphere. After 7 days, the reaction was stopped and the flask was cooled to room temperature. The residue was a high viscosity liquid. The resulting PLGA-PEG-PLGA block copolymer had a weight averaged molecular weight (Mw) of 3910 determined by GPC as described in Example 1.

EXAMPLE 4

This example illustrates the synthesis of a PLA oligomer. An 85% solution of D, L-lactic acid (164g) was heated at 160° C. for 16 hours. Following the incubation a stream of nitrogen is passed through the solution while applying vacuum to remove water and residual lactic acid. The resulting PLA oligomer had a weight averaged molecular weight (Mw) of 1511 determined by GPC. The GPC was performed on two Phenogel columns (300×7.8), 50 Å, and a mixed bed connected in series. Mobile phase was tetrahydrofuran. Calibration was with polystyrene standards. Detection was by refractive index.

EXAMPLE 5

The solution stability enhancing properties of PLA oligomers are illustrated in this example. The PLA oligomers prepared in Example 4 (75 mg) was added to 600 mg of PLGA-PEG-PLGA triblock copolymer prepared in Example 1, 40 mg of paclitaxel, and 2 ml of reverse osmosis deionized water. The mixture was subjected to sonication for 15 minutes, vortexed, and sonicated for an additional 15 minutes. The solution was then filtered through a 0.2 $\mu$m filter. A similar preparation without the PLA oligomers was prepared for comparison. A precipitate appeared within 1 day with the PLGA-PEG-PLGA triblock copolymer system alone, while the solution containing the PLA oligomer maintained paclitaxel in solution and remained clear for more than 3 days.

EXAMPLE 6

Cyclosporin A is another hydrophobic drug that is highly insoluble in water (solubility is approximately 4 $\mu$g/ml). PLA oligomers prepared in Example 4 (75 mg) was added to 600 mg of PLGA-PEG-PLGA triblock copolymer prepared in Example 1, 10 mg of cyclosporin A, and 2 ml of reverse osmosis deionized water. The mixture was subjected to sonication for 15 minutes, vortexed, and sonicated an additional 15 minutes. The mixture was then heated to 60° C. until the drug was dissolved. The solution was filtered through a 0.2 $\mu$m filter. A similar preparation without the PLA oligomers was prepared for comparison. The maximum concentration of cyclosporin A dissolved in the triblock copolymer alone was 2 mg/mL, while concentration of cyclosporin A dissolved in the mixture of PLA oligomer and the triblock copolymer was greater than 10 mg/mL.

EXAMPLE 7

This example illustrates the solubility enhancing effect of the composition of the present invention on the hydrophobic drug nifedipine. The aqueous solubility of nifedipine is 6 µg/mL.

The PLA oligomers prepared in Example 4 (75 mg) was added to 600 mg of PLGA-PEG-PLGA triblock copolymer prepared in Example 1, 100 mg of nifedipine. The mixture was homogenized using a magnetic stir bar at 60° C. A similar preparation without the PLA oligomers was prepared for comparison. Once the mixture had cooled, 1 ml of reverse osmosis deionized water was added to the top of the mixture. Initiation and extent of nifedipine precipitation was recorded. The solution was allowed to equilibrate and the concentration of the nifedipine in the supernatant was measured by HPLC analysis. The concentration of nifedipine in the PLGA-PEG-PLGA triblock copolymer alone was 2 mg/mL, while concentration of nefedipine in the mixture of PLA oligomer and the triblock copolymer was 4 mg/mL. PLA oligomers extended the time prior to nifedipine precipitation from 15 minutes to 4 hours and reduced the extent of the precipitation.

EXAMPLE 8

This example illustrates the solubility enhancing effect of the composition of the present invention on the hydrophobic drug amphotericin B.

The PLA oligomers prepared in Example 4 (113 mg) was added to 900 mg of PLGA-PEG-PLGA triblock copolymer prepared in Example 1, 12 mg of amphotericin B, and 3 mL of dimethyl formamide. A similar preparation without the PLA oligomers was prepared for comparison. The mixture was added to dialysis tubing with a 3500 Dalton molecular weight cutoff and dialyzed against reverse osmosis deionized water (pH=2) overnight. The dialysate was then exchanged for reverse osmosis deionized water and dialyzed overnight. The reported solubility of amphotericin B in water is 3 µg/mL. The solubility of amphotericin B in the triblock copolymer solution of Example 1(entry 1) was measured and was 150 µg/mL. The maximum concentration of amphotericin B in the mixture of PLA oligomers and the triblock copolymer was improved greater then 10 fold than that in the triblock copolymer alone.

EXAMPLE 9

AB diblock copolymers were synthesized by weighing 30 g of PEG-Me (Mw=2000) and transferring it into a 250 mL 3-neck round bottom reaction flask. The oil bath was heated to 155° C. The molten PEG-Me was stirred under vacuum for 3 hours to remove water. The reaction flask was then raised out of the oil bath, the stopcock was closed and the vacuum was released. The stopcock was opened and the headspace was flushed with dry nitrogen.

Twenty-seven grams of D, L-lactide was weighed out and added to the reaction flask. The headspace was evacuated under vacuum, then flushed with dry nitrogen, for a total of 5 cycles.

The flask was then immersed into a 155° C. oil bath. Once the D, L-lactide was melted and the temperature inside the reaction flask reached 150° C., 2 drops (200 ppm) of stannous 2-ethylhexanoate was added to the reaction flask. The reaction was stirred continuously for 8 hours at a rate of 600–700 rpm.

The oil bath temperature was reduced to 140° C., and the reaction flask was attached to vacuum for 40 minutes to remove any unreacted monomer.

The resulting Me-PEG-PLGA copolymer had a weight averaged molecular weight (Mw) of 3323 as measured by GPC. The GPC was performed on two Phenogel columns (300×7.8), 50 Å, and a mixed bed connected in series. Mobile phase was tetrahydrofuran. Calibration was with PEG standards. Detection was by refractive index.

EXAMPLE 10

This example illustrates the solubility enhancing effect of the composition of the present invention with an AB type diblock copolymer on the hydrophobic drug paclitaxel.

The PLA oligomers prepared in Example 4 (75 mg) were added to 600 mg of Me-PEG-PLGA diblock copolymer prepared in Example 9, 40 mg of paclitaxel, and 2 mL of reverse osmosis deionized water. The mixture was subjected to sonication for 15 minutes, vortexed, and sonicated for an additional 15 minutes. The solution was then filtered through a 0.2 µm filter. A similar preparation without the PLA oligomers was prepared for comparison. Precipitate began to appear within 1 day from the Me-PEG-PLGA diblock copolymer system alone, while the solution containing the PLA oligomer maintained paclitaxel in solution and remained clear for more than 2 days.

EXAMPLE 11

BAB triblock copolymers are synthesized by coupling two methoxy-PEG-PLGA diblocks using hexyl diisocynate where the PEG B-block at either end has a Mw of 750 and the A-block has a combined molecular weight between 1500 to 2500 with various lactide and/or glycolide content. Although diblocks can be coupled via ester or urethane, or a combination of ester and urethane links, the copolymers of theis example contained urethane links. The properties of these triblock copolymers are listed in the following Table:

TABLE 4

| Example BAB Block Copolymers with Solubility Enhancing Function | | | |
|---|---|---|---|
| NMR Weight-Averaged Molecular Weight | Weight % A-blocks | PLA:PGA (mole ratio) | Solubilizing Enhancing Function |
| 2640 | 50.1 | 50:50 | yes |
| 4999 | 64 | 75:25 | yes |
| 2640 | 50.1 | 100:0 | yes |
| 4999 | 64 | 100:0 | yes |

All of the PEG-PLGA-PEG triblock copolymers listed in the above table show the solubility enhancing function. In conjunction with PLA oligomers the enhancement is increased further.

The above description will enable one skilled in the art to make composition comprising ABA (e.g., PLGA-PEG-PLGA and PLA-PEG-PLA) or BAB (e.g., PEG-PLGA-PEG and PEG-(PLA-PEG)) type triblock copolymers, AB type diblock copolymers, and PLA/PLGA oligomers that enhance the solubility of hydrophobic drugs and can be used as biodegradable and biocompatible solubilizing agents in the field of drug delivery. Although the enhanced solubility of a few hydrophobic drugs are illustrated in the examples to show the functionality of the compositions of the present invention, these descriptions are not intended to be an exhaustive statement of all drugs whose solubility can be enhanced by the composition of the present invention. Certainly, numerous other drugs from various categories of therapeutic agents are well suited for forming aqueous solutions of the composition of PLA/PLGA oligomers and triblock or diblock copolymers as described in this invention. Neither are all block copolymers shown which may be prepared, and which demonstrate the property of enhancing the solubility of a drug. However, it will be immediately apparent to one skilled in the art that various modifications may be made without departing from the scope of the invention that is limited only by the following claims and their functional equivalents.

We claim:

1. A polymeric composition having improved capability of solubilizing a drug in a hydrophilic environment, comprising:
   1) a biodegradable polyester oligomer having a weight averaged molecular weight of between 400 and 10,000 daltons; and
   2) a biodegradable AB-type, ABA-type, or BAB-type block copolymer, comprising:
      i) 50.1 to 65% by weight of a biodegradable, hydrophobic A polymer block comprising a biodegradable polyester, and
      ii) 35 to 49.9% by weight of a hydrophilic B polymer block comprising a polyethylene glycol (PEG), and wherein the block copolymer has a weight averaged molecular weight of between 2400 to 4999 daltons, wherein said composition is soluble in aqueous environment.

2. The polymeric composition according to claim 1 wherein the biodegradable polyester oligomer is synthesized from monomers selected from the group consisting of D, L-lactide, D-Lactide, L-lactide, D, L-lactic acid, D-lactic acid, L-lactic acid, glycolide, glycolic acid, ε-caprolactone, ε-hydroxy hexanoic acid, and copolymers thereof.

3. The polymeric composition according to claim 1 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof.

4. The polymeric composition according to claim 1 wherein the biodegradable polyester of the A-block of the copolymer is different from the biodegradable polyester of the oligomer.

5. The polymeric composition according to claim 1 wherein the A polymer block and oligomer comprise between about 20 to 100 mole percent lactide or lactic acid, and between about 0 to 80 mole percent glycolide or glycolic acid.

6. The polymeric composition according to claim 1 wherein the content of the biodegradable polyester oligomer of said composition is within a range of 0.01% to 30% by weight of the total polymer mixture, and the content of the biodegradable AB-type, ABA-type, or BAB-type block copolymer is within a range of 70% to 99.99% by weight of the total polymer mixture.

7. A biodegradable polymeric drug delivery composition capable of solubilizing drug in a hydrophilic environment, comprising:
   (a) an effective amount of a drug;
   (b) a biodegradable polyester oligomer with a weight averaged molecular weight of 400 to 10,000 daltons; and
   (c) a biodegradable AB-type, ABA-type, or BAB-type block copolymer comprising:
      i) 50.1 to 65% by weight of a biodegradable, hydrophobic A polymer block comprising a biodegradable polyester, and
      ii) 35 to 49.9% by weight of a hydrophilic B polymer block comprising a polyethylene glycol (PEG), and wherein the block copolymer has a weight-averaged molecular weight of between 2400 to 4999, wherein said composition is soluble in aqueous environment.

8. The polymeric drug delivery composition according to claim 7 wherein the content of the biodegradable polyester oligomer of said composition is within a range of 0.01% to 30% by weight of the total polymer mixture, and the content of the biodegradable AB-type, ABA-type, or BAB-type block copolymer is within a range of 70% to 99.99% by weight of the total polymer mixture.

9. The polymeric drug delivery composition according to claim 7 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof.

10. The polymeric drug delivery composition according to claim 7 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof.

11. The polymeric drug delivery composition according to claim 7 wherein the biodegradable polyester of the A-block of the copolymer is different from the biodegradable polyester of the oligomer.

12. The polymeric drug delivery composition according to claim 7 wherein the A polymer block and oligomer comprise between about 20 to 100 mole percent lactide or lactic acid, and between about 0 to 80 mole percent glycolide or glycolic acid.

13. The polymeric drug delivery composition according to claim 7 wherein the drug content is $10^{-6}$ to 100% of the total polymer weight.

14. A biodegradable polymeric composition as a drug delivery vehicle capable of solubilizing drug in a hydrophilic environment, comprising:
   (a) a biodegradable polyester oligomer with a weight averaged molecular weight of 400 to 10,000 daltons; and
   (b) a biodegradable AB-type, ABA-type, or BAB-type block copolymer comprising:
      i) 50.1 to 65% by weight of a biodegradable, hydrophobic A polymer block comprising a biodegradable polyester, and
      ii) 35 to 49.9% by weight of a hydrophilic B polymer block comprising a polyethylene glycol (PEG), and wherein the block copolymer has a weight-averaged molecular weight of between 2400 to 4999; and
   (c) an aqueous solution, wherein said composition is soluble in aqueous environment.

15. The biodegradable polymeric drug delivery vehicle according to claim 14 wherein the content of the biodegradable polyester oligomer of said composition is within a range of 0.01% to 30% by weight of the total polymer mixture, and the content of the biodegradable AB-type, ABA-type, or BAB-type block copolymer is within a range of 70% to 99.99% by weight of the total polymer mixture.

16. The biodegradable polymeric drug delivery vehicle according to claims 14 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, ϵ-caprolactone, ϵ-hydroxy hexanoic acid, and copolymers thereof.

17. The biodegradable polymeric drug delivery vehicle according to claim 14 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, ϵ-caprolactone, ϵ-hydroxy hexanoic acid, and copolymers thereof.

18. The biodegradable polymeric drug delivery vehicle according to claim 14 wherein the biodegradable polyester of the A-block of the copolymer is different from the biodegradable polyester of the oligomer.

19. The biodegradable polymeric drug delivery vehicle according to claim 14 wherein the A polymer block and oligomer comprise between about 20 to 100 mole percent lactide or lactic acid, and between about 0 to 80 mole percent glycolide or glycolic acid.

20. The biodegradable polymeric drug delivery vehicle according to claim 14 further comprising a member selected from the group consisting of excipients, additives, buffers, osmotic pressure adjusting agents, antioxidants, preservatives and drug stabilizing agents.

21. The biodegradable polymeric drug delivery vehicle according to claim 14 wherein the block copolymer content is 1% to 50% of the total weight of biodegradable polymeric drug delivery vehicle.

22. A biodegradable aqueous drug solution comprising:
    (a) an effective amount of a drug;
    (b) a biodegradable polyester oligomer with weight averaged molecular weight of 400 to 10,000 daltons; and
    (c) a biodegradable AB-type, ABA-type, or BAB-type block copolymer capable of solubilizing said drug in a hydrophilic environment, comprising:
        i) 50.1 to 65% by weight of a biodegradable, hydrophobic A polymer block comprising a biodegradable polyester, and
        ii) 35 to 49.9% by weight of a hydrophilic B polymer block comprising a polyethylene glycol (PEG), and wherein the tri-block copolymer has a weight-averaged molecular weight of between 2400 to 4999; and
    (d) an aqueous solution.

23. The biodegradable polymeric drug delivery vehicle according to claim 22 further comprising a member selected from the group consisting of excipients, additives, buffers, osmotic pressure adjusting agents, antioxidants, preservatives and drug stabilizing agents.

24. The biodegradable aqueous drug solution according to claim 22 wherein the copolymer content is 1% to 50% of the total weight of the aqueous drug solution.

25. The biodegradable aqueous drug solution according to claim 22 wherein the drug content is $10^{-6}$ to 100% of the total polymer weight.

26. The biodegradable aqueous drug solution according to claim 22 wherein the content of the biodegradable polyester oligomer of said composition is within a range of 0.01% to 30% by weight of the total polymer mixture, and the content of the biodegradable AB-type, ABA-type, or BAB-type block copolymer is within a range of 70% to 99.99% by weight of the total polymer mixture.

27. The biodegradable aqueous polymeric drug solution according to claims 22 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, ϵ-caprolactone, ϵ-hydroxy hexanoic acid, and copolymers thereof.

28. The biodegradable aqueous polymeric drug solution according to claim 22 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, ϵ-caprolactone, ϵ-hydroxy hexanoic acid, and copolymers thereof.

29. The biodegradable aqueous polymeric drug solution according to claim 22 wherein the biodegradable polyester of the A-block of the copolymer is different from the biodegradable polyester of the oligomer.

30. The biodegradable aqueous drug solution according to claim 22 wherein the A-block and the oligomer comprise between about 20 to 100 mole percent lactide or lactic acid and between about 0 to 80 mole percent glycolide or glycolic acid.

31. A method for administering a drug to a warm blooded animal, comprising
    administering to a warm blooded animal a biodegradable polymeric drug delivery composition, said composition comprising:
        (a) an effective amount of a drug;
        (b) a biodegradable polyester oligomer with a weight averaged molecular weight of 400 to 10,000 daltons; and
        (c) a biodegradable AB-type, ABA-type, or BAB-type block copolymer comprising:
            i) 50.1 to 65% by weight of a biodegradable, hydrophobic A polymer block comprising a biodegradable polyester, and
            ii) 35 to 49.9% by weight of a hydrophilic B polymer block comprising a polyethylene glycol (PEG), and wherein the block copolymer has a weight-averaged molecular weight of between 2400 to 4999, wherein said composition is soluble in aqueous environment.

32. The method according to claim 31 wherein the content of the biodegradable polyester oligomer of said composition is within a range of 0.01% to 30% by weight of the total polymer mixture, and the content of the biodegradable AB-type, ABA-type, or BAB-type block copolymer is within a range of 70% to 99.99% by weight of the total polymer mixture.

33. The method according to claims 31 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, ϵ-caprolactone, ϵ-hydroxy hexanoic acid, and copolymers thereof.

34. The method according to claim 31 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, ϵ-caprolactone, ϵ-hydroxy hexanoic acid, and copolymers thereof.

35. The method according to claim 31 wherein the biodegradable polyester of the A-block of the copolymer is different from the biodegradable polyester of the oligomer.

36. The method according to claim 31 wherein the A polymer block and oligomer comprise between about 20 to 100 mole percent lactide or lactic acid, and between about 0 to 80 mole percent glycolide or glycolic acid.

37. The method according to claim 31 wherein the drug content is $10^{-6}$ to 100% of the total polymer weight.

38. The method according to claim 31 wherein said administration is by parenteral, ocular, topical, inhalation, transdermal, vaginal, buccal, transmucosal, transurethral, rectal, nasal, oral, peroral, pulmonary or aural means.

39. A method for administering a drug to a warm blooded animal, comprising
   1) preparing a biodegradable aqueous drug solution comprising:
      (a) an effective amount of a drug;
      (b) a biodegradable polyester oligomer with weight averaged molecular weight of 400 to 10,000 daltons;
      (c) a biodegradable AB-type, ABA-type, or BAB-type block copolymer capable of solubilizing said drug in a hydrophilic environment, comprising:
         i) 50.1 to 65% by weight of a biodegradable, hydrophobic A polymer block comprising a biodegradable polyester, and
         ii) 35 to 49.9% by weight of a hydrophilic B polymer block comprising a polyethylene glycol(PEG), and wherein the tri-block copolymer has a weight-averaged molecular weight of between 2400 to 4999; and
      (d) an aqueous solution; and
   2) administering said biodegradable aqueous drug solution to a warm blooded animal.

40. The method according to claim 39 wherein the block copolymer content is 1% to 50% of the total weight of the aqueous drug solution.

41. The method according to claim 39 wherein the content of the biodegradable polyester oligomer is within a range of 0.01% to 30% by weight of the total polymer mixture, and the content of the biodegradable AB-type, ABA-type, or BAB-type block copolymer is within a range of 70% to 99.99% by weight of the total polymer mixture.

42. The method according to claim 39 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof.

43. The method according to claim 39 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof.

44. The method according to claim 39 wherein the biodegradable polyester of the A-block of the copolymer is different from the biodegradable polyester of the oligomer.

45. The method according to claim 39 wherein the A-block and oligomer comprise between about 20 to 100 mole percent lactide or lactic acid and between about 0 to 80 mole percent glycolide or glycolic acid.

46. The method according to claim 39 wherein the drug content is $10^{-6}$ to 100% of the total polymer weight.

47. The method according to claim 39 wherein said administration is by parenteral, ocular, topical, inhalation, transdermal, vaginal, buccal, transmucosal, transurethral, rectal, nasal, oral, peroral, pulmonary or aural means.

48. A method for enhancing the solubility of a drug in aqueous environment, comprising
   1) preparing a polymeric composition comprising: a biodegradable polyester oligomer having a weight averaged molecular weight of between 400 and 10,000 daltons; and a biodegradable AB-type, ABA-type, or BAB-type block copolymer, comprising:
      i) 50.1 to 65% by weight of a biodegradable, hydrophobic A polymer block comprising a biodegradable polyester, and
      ii) 35 to 49.9% by weight of a hydrophilic B polymer block comprising a polyethylene glycol (PEG), and wherein the block copolymer has a weight averaged molecular weight of between 2400 to 4999 daltons;
   2) admixing the polymeric composition with a drug; and
   3) admixing the drug containing polymeric composition with an aqueous solution to obtain a drug solution.

49. The method according to claim 48 wherein the block copolymer content is 1% to 50% of the total weight of the aqueous drug solution.

50. The method according to claim 48 wherein the content of the biodegradable polyester oligomer is within a range of 0.01% to 30% by weight of the total polymer mixture, and the content of the biodegradable AB-type, ABA-type, or BAB-type block copolymer is within a range of 70% to 99.99% by weight of the total polymer mixture.

51. The method according to claim 48 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof.

52. The method according to claim 48 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, ε-caprolactone, ε-hydroxy hexanoic acid, and copolymers thereof.

53. The method according to claim 48 wherein the biodegradable polyester of the A-block of the copolymer is different from the biodegradable polyester of the oligomer.

54. The method according to claim 48 wherein the A-block and oligomer comprise between about 20 to 100 mole percent lactide or lactic acid and between about 0 to 80 mole percent glycolide or glycolic acid.

55. The method according to claim 48 wherein the drug content is $10^{-6}$ to 100% of the total polymer weight.

56. A method for enhancing the solubility of a drug in aqueous environment, comprising
   1) preparing a polymeric composition comprising: a biodegradable polyester oligomer having a weight averaged molecular weight of between 400 and 10,000 daltons; and a biodegradable AB-type, ABA-type, or BAB-type block copolymer, comprising:
      i) 50.1 to 65% by weight of a biodegradable, hydrophobic A polymer block comprising a biodegradable polyester, and
      ii) 35 to 49.9% by weight of a hydrophilic B polymer block comprising a polyethylene glycol (PEG), and wherein the block copolymer has a weight averaged molecular weight of between 2400 to 4999 daltons;
   2) admixing said composition with an aqueous solution to form a polymeric solution, and
   3) admixing said polymer solution with a drug to form a drug solution.

57. The method according to claim 56 wherein the block copolymer content is 1% to 50% of the total weight of the aqueous drug solution.

58. The method according to claim 56 wherein the content of the biodegradable polyester oligomer is within a range of 0.01% to 30% by weight of the total polymer mixture, and the content of the biodegradable AB-type, ABA-type, or BAB-type block copolymer is within a range of 70% to 99.99% by weight of the total polymer mixture.

59. The method according to claim 56 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, $\epsilon$-caprolactone, $\epsilon$-hydroxy hexanoic acid, and copolymers thereof.

60. The method according to claim 56 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, $\epsilon$-caprolactone, $\epsilon$-hydroxy hexanoic acid, and copolymers thereof.

61. The method according to claim 56 wherein the biodegradable polyester of the A-block of the copolymer is different from the biodegradable polyester of the oligomer.

62. The method according to claim 56 wherein the A-block and oligomer comprise between about 20 to 100 mole percent lactide or lactic acid and between about 0 to 80 mole percent glycolide or glycolic acid.

63. The method according to claim 56 wherein the drug content is $10^{-6}$ to 100% of the total polymer weight.

64. A method for stabilizing a drug in aqueous environment, comprising
   1) preparing a polymeric composition comprising: a biodegradable polyester oligomer having a weight averaged molecular weight of between 400 and 10,000 daltons; and a biodegradable AB-type, ABA-type, or BAB-type block copolymer, comprising:
      i) 50.1 to 65% by weight of a biodegradable, hydrophobic A polymer block comprising a biodegradable polyester, and
      ii) 35 to 49.9% by weight of a hydrophilic B polymer block comprising a polyethylene glycol (PEG), and wherein the block copolymer has a weight averaged molecular weight of between 2400 to 4999 daltons;
   2) admixing said composition with aqueous solution to form a polymeric solution, and
   3) admixing said polymer solution with a drug to form a drug solution.

65. The method according to claim 64 wherein the block copolymer content is 1% to 99% of the total weight of the aqueous drug solution.

66. The method according to claim 64 wherein the content of the biodegradable polyester oligomer is within a range of 0.01% to 30% by weight of the total polymer mixture, and the content of the biodegradable AB-type, ABA-type, or BAB-type block copolymer is within a range of 70% to 99.99% by weight of the total polymer mixture.

67. The method according to claim 64 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, $\epsilon$-caprolactone, $\epsilon$-hydroxy hexanoic acid, and copolymers thereof.

68. The method according to claim 64 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, $\epsilon$-caprolactone, $\epsilon$-hydroxy hexanoic acid, and copolymers thereof.

69. The method according to claim 64 wherein the biodegradable polyester of the A-block of the copolymer is different from the biodegradable polyester of the oligomer.

70. The method according to claim 64 wherein the A-block and oligomer comprise between about 20 to 100 mole percent lactide or lactic acid and between about 0 to 80 mole percent glycolide or glycolic acid.

71. The method according to claim 64 wherein the drug content is $10^{-6}$ to 100% of the total polymer weight.

72. A method for enhancing the solubility of a drug in aqueous environment, comprising
   1) preparing a polymeric composition comprising: a biodegradable polyester oligomer having a weight averaged molecular weight of between 400 and 10,000 daltons; and a biodegradable AB-type, ABA-type, or BAB-type block copolymer, comprising:
      i) 50.1 to 65% by weight of a biodegradable, hydrophobic A polymer block comprising a biodegradable polyester, and
      ii) 35 to 49.9% by weight of a hydrophilic B polymer block comprising a polyethylene glycol (PEG), and wherein the block copolymer has a weight averaged molecular weight of between 2400 to 4999 daltons;
   2) admixing a drug with an aqueous solution to form a drug-aqueous solution mixture, and
   3) admixing said polymer solution with said drug-aqueous solution mixture to form a polymeric aqueous drug solution.

73. The method according to claim 72 wherein the block copolymer content is 1% to 50% of the total weight of the aqueous drug solution.

74. The method according to claim 72 wherein the content of the biodegradable polyester oligomer is within a range of 0.01% to 30% by weight of the total polymer mixture, and the content of the biodegradable AB-type, ABA-type, or BAB-type block copolymer is within a range of 70% to 99.99% by weight of the total polymer mixture.

75. The method according to claim 72 wherein the biodegradable polyester oligomer is synthesized from monomers selected from the group consisting of D, L-lactide, D-lactide, L-lactide, D, L-lactic acid, D-lactic acid, L-lactic acid, glycolide, glycolic acid, $\epsilon$-caprolactone, $\epsilon$-hydroxy hexanoic acid, and copolymers thereof.

76. The method according to claim 72 wherein the biodegradable polyester of the hydrophobic A polymer block is synthesized from monomers selected from the group consisting of D, L-lactide, D-lactide, L-lactide, D, L-lactic acid, D-lactic acid, L-lactic acid, glycolide, glycolic acid, $\epsilon$-caprolactone, $\epsilon$-hydroxy hexanoic acid, and copolymers thereof.

77. The method according to claim 72 wherein the biodegradable polyester of the A-block of the copolymer is different from the biodegradable polyester of the oligomer.

78. The method according to claim 72 wherein the A-block and oligomer comprise between about 20 to 100 mole percent lactide or lactic acid and between about 0 to 80 mole percent glycolide or glycolic acid.

79. The method according to claim 72 wherein the drug content is $10^{-6}$ to 100% of the total polymer weight.

* * * * *